(12) United States Patent
Jamali et al.

(10) Patent No.: US 8,544,751 B2
(45) Date of Patent: Oct. 1, 2013

(54) SYSTEM AND METHOD FOR MANAGING A MEDICAL PROCEDURE SITE WITH A MACHINE READABLE MARKING

(76) Inventors: Mehrnaz Nicole Jamali, Dana Point, CA (US); Amir Saied Ghanouni, Tustin, CA (US)

( * ) Notice: Subject to any disclaimer, the term of this patent is extended or adjusted under 35 U.S.C. 154(b) by 267 days.

(21) Appl. No.: 12/844,715

(22) Filed: Jul. 27, 2010

(65) Prior Publication Data

US 2011/0024491 A1    Feb. 3, 2011

Related U.S. Application Data

(60) Provisional application No. 61/230,992, filed on Aug. 3, 2009.

(51) Int. Cl.
*G06K 19/00* (2006.01)
(52) U.S. Cl.
USPC .................. 235/487; 235/375; 235/462.01
(58) Field of Classification Search
USPC ..................................... 235/487, 375, 462.01
See application file for complete search history.

(56) References Cited

U.S. PATENT DOCUMENTS

| | | | |
|---|---|---|---|
| 4,857,716 A | 8/1989 | Gombrich et al. | |
| 5,443,082 A | 8/1995 | Mewburn | |
| 5,610,811 A | 3/1997 | Honda | |
| 6,081,741 A | 6/2000 | Hollis | |
| 6,641,039 B2 | 11/2003 | Southhard | |
| 6,648,223 B2 | 11/2003 | Boukhny et al. | |
| 7,389,928 B2 | 6/2008 | Lubow | |
| 7,540,287 B2 | 6/2009 | Chole | |
| 2003/0184081 A1 | 10/2003 | Carlson, II | |
| 2003/0187458 A1 | 10/2003 | Carlson, II | |
| 2004/0056478 A1 | 3/2004 | Bruce | |
| 2004/0225282 A1 | 11/2004 | Ness | |
| 2005/0279368 A1 | 12/2005 | McCombs | |
| 2006/0138211 A1* | 6/2006 | Lubow | 235/375 |
| 2006/0168211 A1 | 7/2006 | Koike | |
| 2008/0077444 A1 | 3/2008 | MacLeod | |
| 2008/0091243 A1 | 4/2008 | Ternes | |

OTHER PUBLICATIONS

International Search Report dated Oct. 6, 2010 from corresponding PCT application No. PCT/US/10/44010.

* cited by examiner

*Primary Examiner* — Allyson Trail
(74) *Attorney, Agent, or Firm* — Salehi Law Group

(57) ABSTRACT

A system for ensuring the correct location/side of a surgery is described. The system includes a reader coupled to a validater. A first machine readable marking associated with a medical procedure site on a body of a patient is placed on a planned medical procedure site on the body of the patient. A second machine readable marking associated with a pre-identified reference point. A reader reads the first and second machine readable marking. A validater receives medical procedure plan data associated with the patient and compares the medical procedure plan data with the first and second machine readable markings to verify the validity of the planned medical procedure and the site of the planned medical procedure.

28 Claims, 13 Drawing Sheets

SYSTEM AND METHOD FOR MANAGING A MEDICAL PROCEDURE SITE WITH A MACHINE READABLE MARKING

RELATED APPLICATIONS

The present application claims priority from U.S. Provisional Patent Application Ser. No. 61/230,992 filed Aug. 3, 2009.

TECHNICAL FIELD

Embodiments of the present invention relate to medical devices, and more particularly, to a medical procedure site identification system.

BACKGROUND

Wrong side surgeries are increasing every year despite behavioral requirements by operative staff and time out procedures. Surgical sites can be marked by surgeon, patient and surgical nurse and yet mistakes are persistent.

A need exists for a system for ensuring that surgeries are performed on the correct side of a patient.

BRIEF DESCRIPTION OF THE DRAWINGS

The present invention is illustrated by way of example, and not by way of limitation, in the figures of the accompanying drawings and in which.

DETAILED DESCRIPTION

Described herein is a system for verifying a surgery site or medical procedure location for ensuring surgery or medical procedure on a correct side of a body of a patient. The system includes a reader coupled to a validater. A first machine readable marking associated with a medical procedure site on a body of a patient is placed on a planned medical procedure site on the body of the patient. A second machine readable marking associated with a pre-identified reference point allows a reader to determine an orientation. In one embodiment, the pre-identified reference point is on a part of the body of the patient on the left or right side of the patient. A reader reads the first and second machine readable marking. A validater receives medical procedure plan data associated with the patient and compares the medical procedure plan data with the first and second machine readable markings to verify the validity of the planned medical procedure site.

Figure 1:
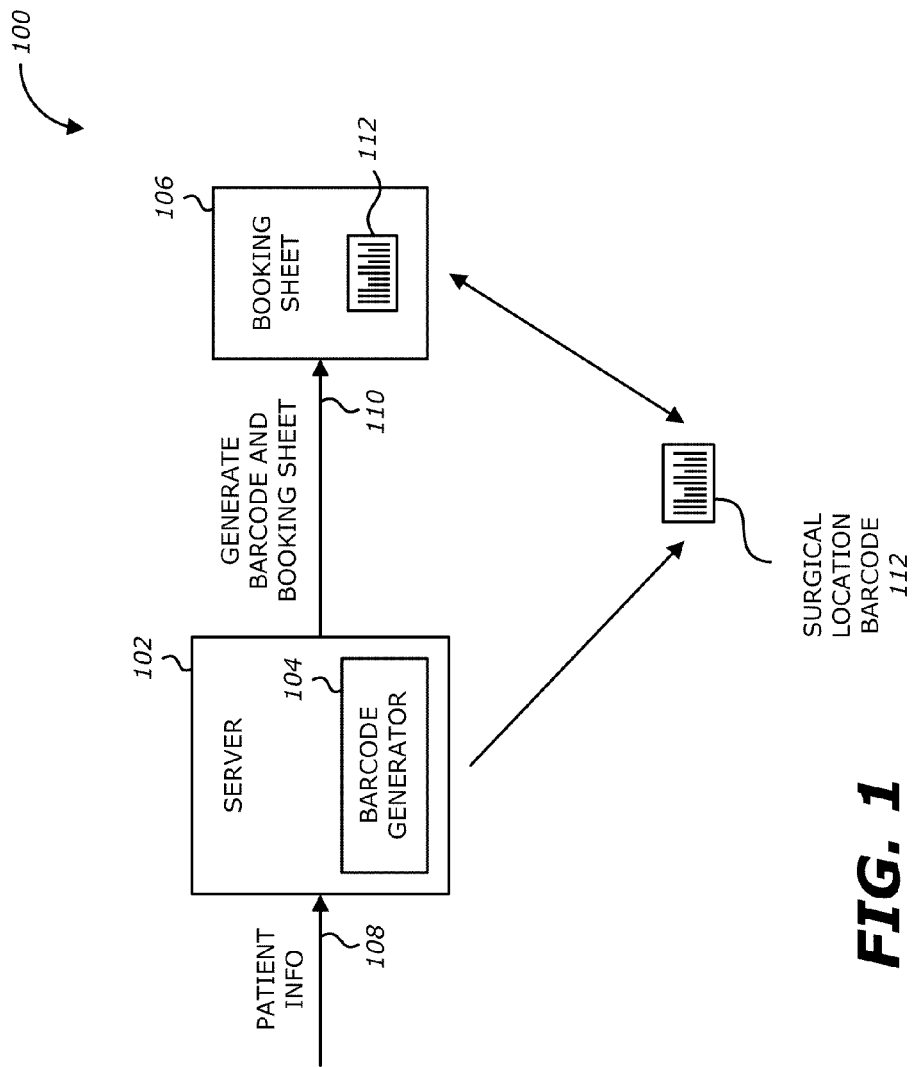
FIG. 1 is a block diagram illustrating one embodiment of a system for generating a booking sheet used to validate a surgery site prior to surgery.

FIG. 1 is a block diagram illustrating one embodiment of a system 100 for generating a booking sheet 106 used to validate the site of a medical procedure such as a surgery site. Prior to surgery, for example, at a doctor office or at the registration office of a hospital, information 108 about a patient is entered into a computing device such as a server 102. The patient information includes and is not limited to a booking number, the name of the patient, date of birth, sex, address, telephone numbers, hospital, surgeon name, date of surgery, nature of medical procedure, and side of which the medical procedure is to be performed among others. Additional information can include allergies, insurance information, and diagnosis codes, etc . . . .

Server 102 includes a barcode generator 104 that is used to generate a barcode on booking sheet 106. In one embodiment, barcode generator 104 includes any software or hardware system commonly used to generate barcodes or other machine readable markings. Booking sheet 106 includes a uniquely generated barcode 112 associated with the patient information. Those of ordinary skills in the art will recognize that the server 102 is not limited to generate barcodes but also any other machine readable marking such as Radio Frequency Identification (RFID), an optical machine readable marking, or a microchip. The barcode 112 may be in the form of a sticker or tag affixed to the booking sheet 106.

In one embodiment, booking sheet 106 is generated prior to the surgery or medical procedure at the hospital where the surgery or medical procedure is to take place. For example, booking sheet 106 may be generated at registration of the patient.

Figure 2:
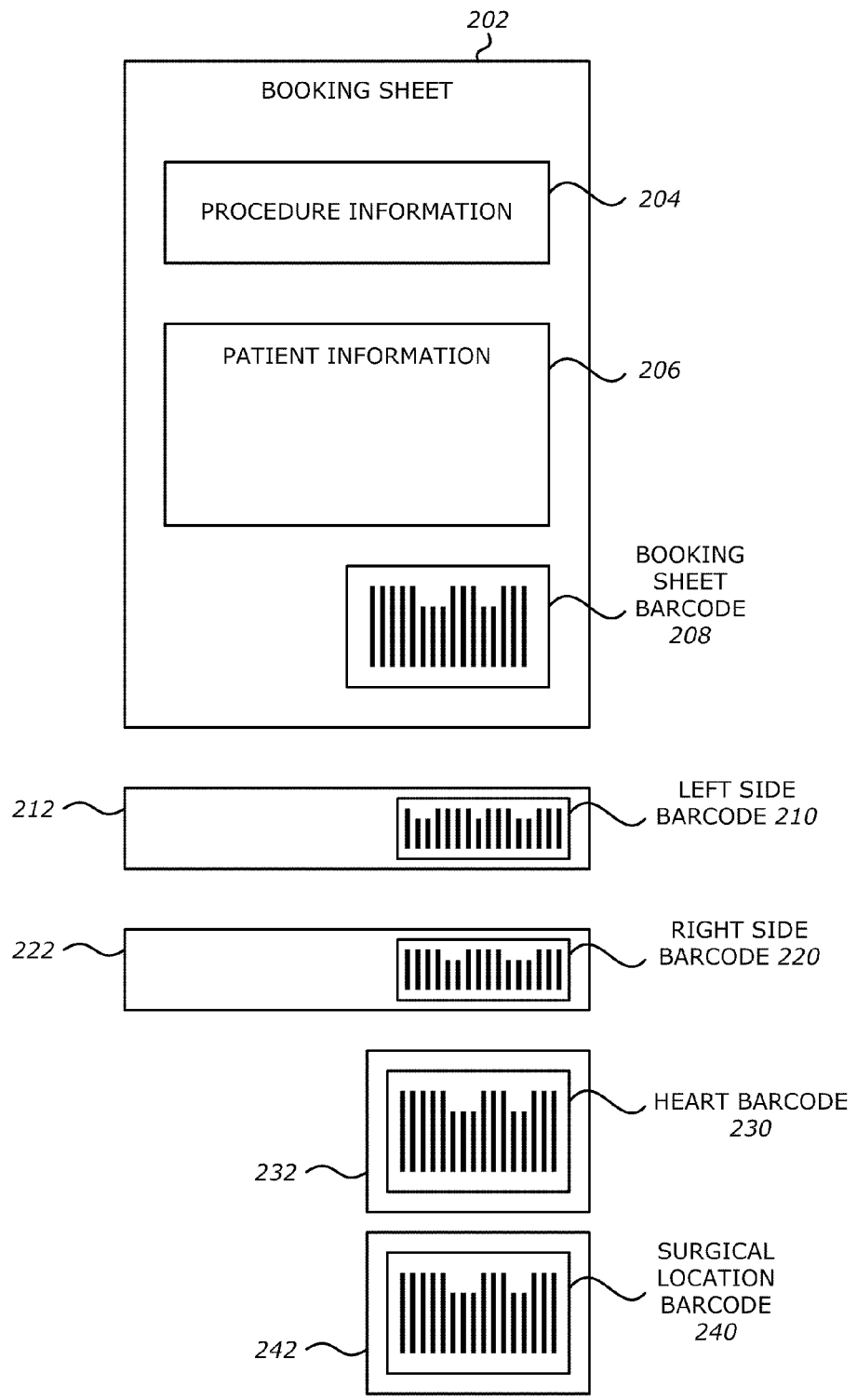
FIG. 2 is a block diagram illustrating one embodiment of barcode tags for a system for verifying a surgery site.

FIG. 2 is a block diagram illustrating one embodiment of a booking sheet 202 and barcode tags used in a system for verifying the site of medical procedure on the body of a patient. Booking sheet 202 includes, for example, surgery procedure information 204 (when, where, what), patient information 206 (who), and booking sheet barcode 208. In one embodiment, booking sheet barcode 208 is generated by barcode generator of server 102. Booking sheet barcode 208 uniquely identifies the information set forth in booking sheet 202. As such, every booking sheet barcode 208 is unique for every patient and every surgery.

A left side barcode 210 identifying a left side of the body of the patient is placed on a tag 212. A right side barcode 220 identifying a right side of the body of the patient is placed on a tag 222. A heart barcode 230 identifying a heart of the patient is affixed to an adhesive film 232 (e.g. a sticker). A surgical location barcode 240 identifying the surgery site of the patient as specified in booking sheet 202 is affixed to an adhesive film 242 (e.g. a sticker). In one embodiment, surgical location barcode 240 and booking sheet barcode 208 are the same. In another embodiment, surgical location barcode 240 and booking sheet barcode 208 are unique and different. Both surgical location barcode 240 and booking sheet barcode 208 are generated by bar code generator 104 of server 102.

In one embodiment, barcodes 210, 220, and 230 are generic or standard barcodes. In other words, all left side barcodes used to identify a left side of the body of the patient are the same. All right side barcodes used to identify a right side of the body of the patient are the same. All heart barcodes used to identify the heart of the patient are the same.

Figure 3A:
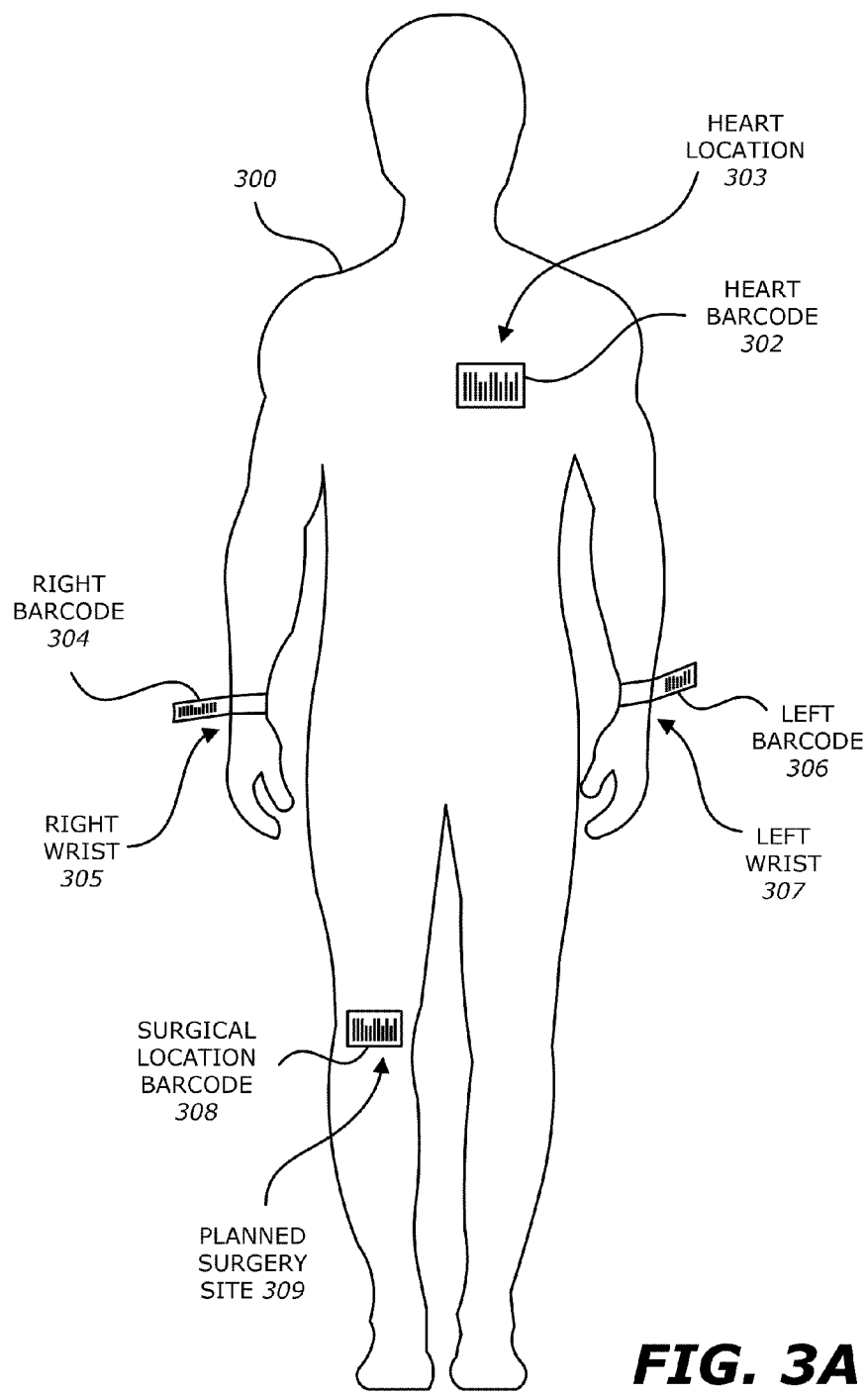
FIG. 3A is a diagram illustrating one embodiment of barcode tags placed on a body of a patient.

FIG. 3A is a diagram illustrating a first embodiment of barcode tags or stickers placed on a body of a patient 300. A heart barcode sticker 302 identifying the heart is placed on the heart location 303 on the chest of patient 300. A right side barcode tag 304 identifying the right wrist/side of patient 300 is affixed to the right wrist 305 of patient 300. A left side barcode tag 306 identifying the left wrist/side of patient 300 is affixed to the left wrist 307 of patient 300. In another embodiment, right and left side barcode tags 304 and 306 may be affixed to other limbs of patient 300 such as ankles, arms, or feet.

A surgery location barcode sticker 308 identifying the surgery location is placed on the planned surgery site 309 of the patient 300. The planned surgery site is the location where the surgeon is planning to operate on. It may or may not be the actual surgery site prescribed in booking sheet 202. Thus, the term planned surgery site is used to distinguish from the surgery site as prescribed by the surgeon in the booking sheet.

In one embodiment, the barcode tags and stickers may be placed prior to the surgery in a pre-operating room or in the operating room.

Figure 3B:
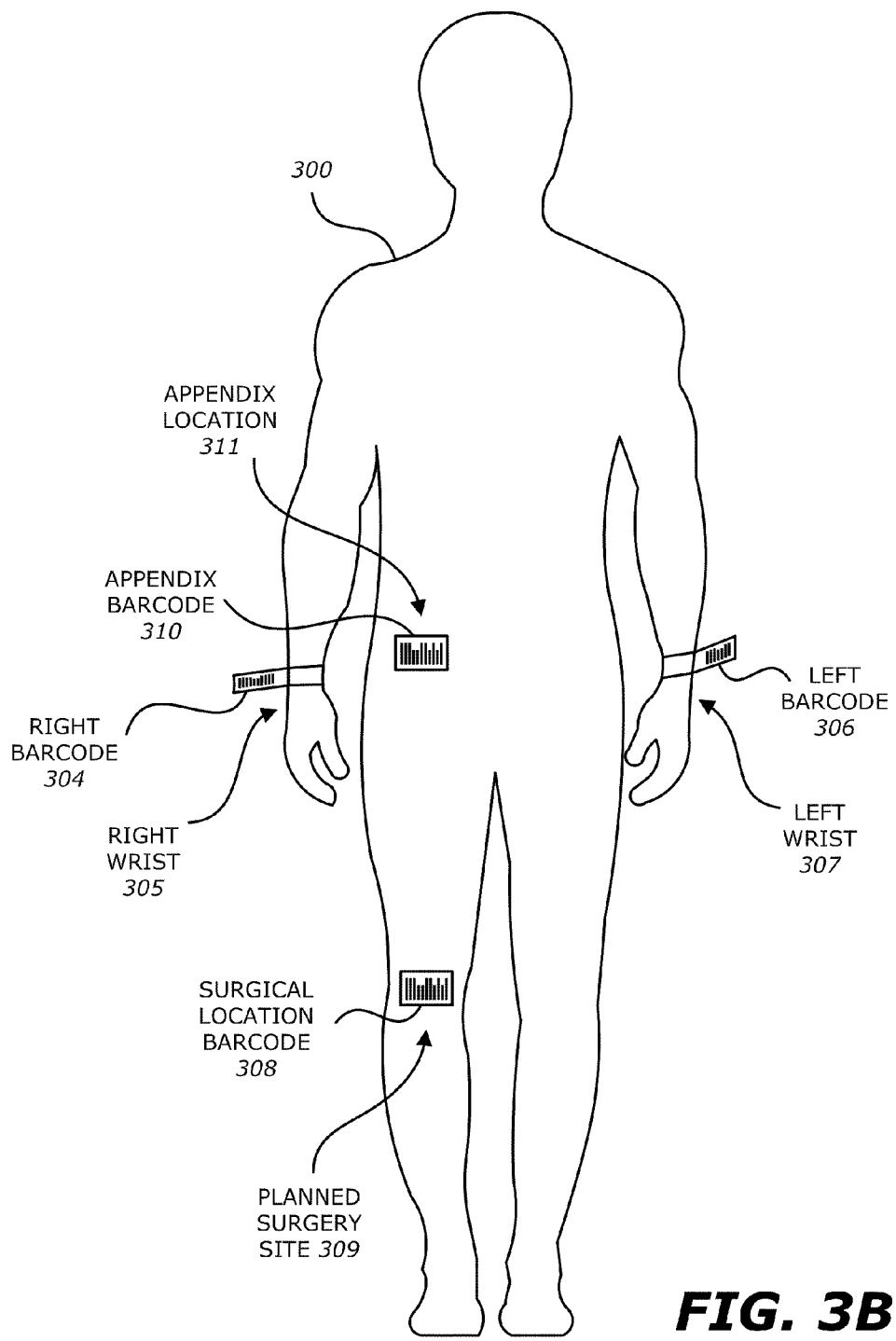
FIG. 3B is a diagram illustrating another embodiment of barcode tags placed on a body of a patient.

FIG. 3B is a diagram illustrating a second embodiment of barcode tags or stickers placed on a body of patient 300. A barcode sticker may be placed on another uniquely identifiable organ besides the heart. The organ needs to permanently resides on only one side of the body of patient 300. For example, instead of the heart, a barcode sticker 310 identifying an appendix is placed on the appendix location 311 of patient 300. Right side barcode tag 304 identifying the right wrist/side of patient 300 is affixed to right wrist 305 of patient 300. Left side barcode tag 306 identifying the left wrist/side of patient 300 is affixed to left wrist 307 of patient 300. Barcode sticker 308 identifying the surgery location is placed on planned surgery site 309 of the patient 300.

Figure 3C:
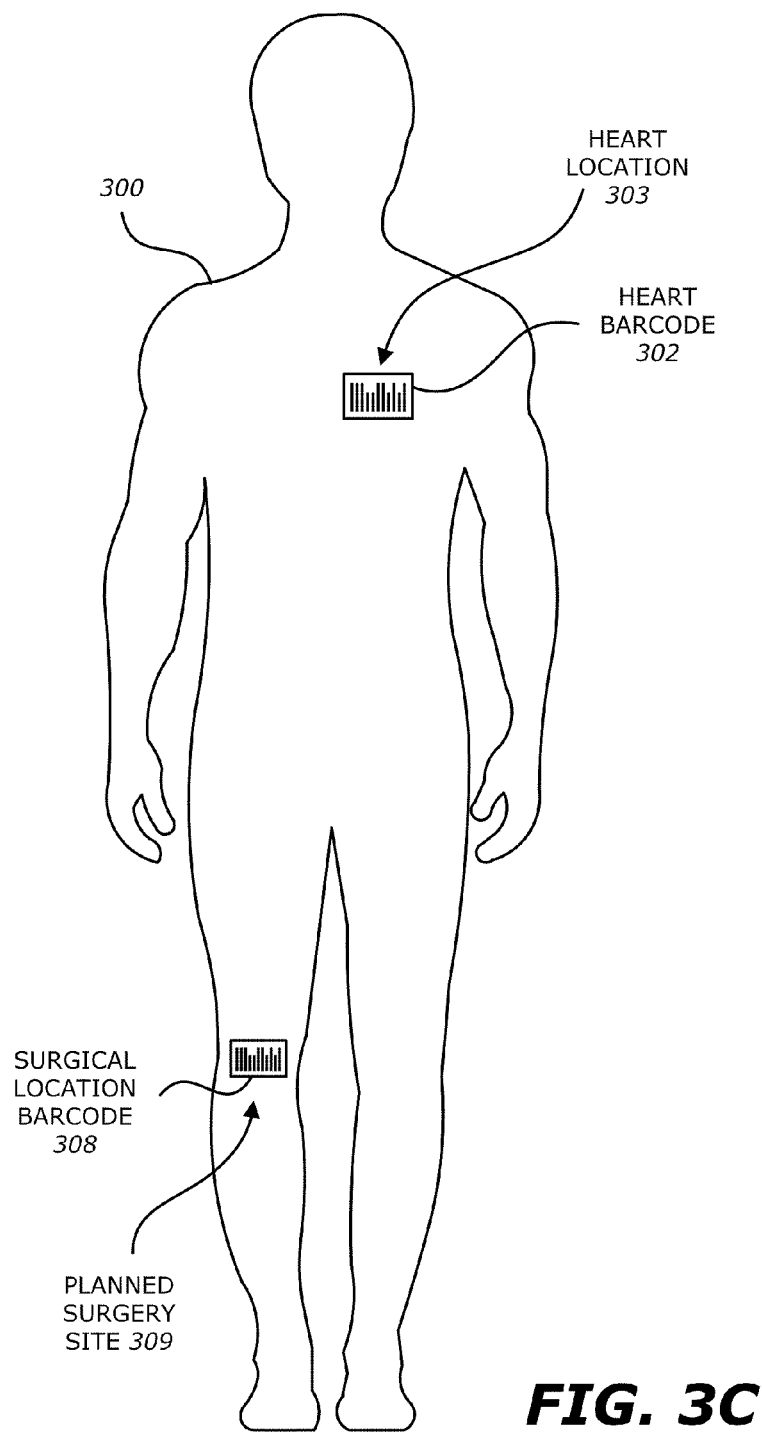
FIG. 3C is a diagram illustrating another embodiment of barcode tags placed on a body of a patient.

FIG. 3C is a diagram illustrating a third embodiment of barcode tags or stickers placed on a body of patient 300. In this embodiment, only two barcode stickers 302 and 308 are used to determine and verify the planned surgery site 309.

In a fourth embodiment, a first and a second barcode sticker are used. The first barcode sticker is placed on the planned surgery site 309 on the patient. The second barcode sticker is placed on a pre-defined reference point such as a left or right side of a limb of the patient, a left or right side of the operating table on which the patient is placed, or any other predetermined reference point to the left or right of the patient's body.

Figure 4:
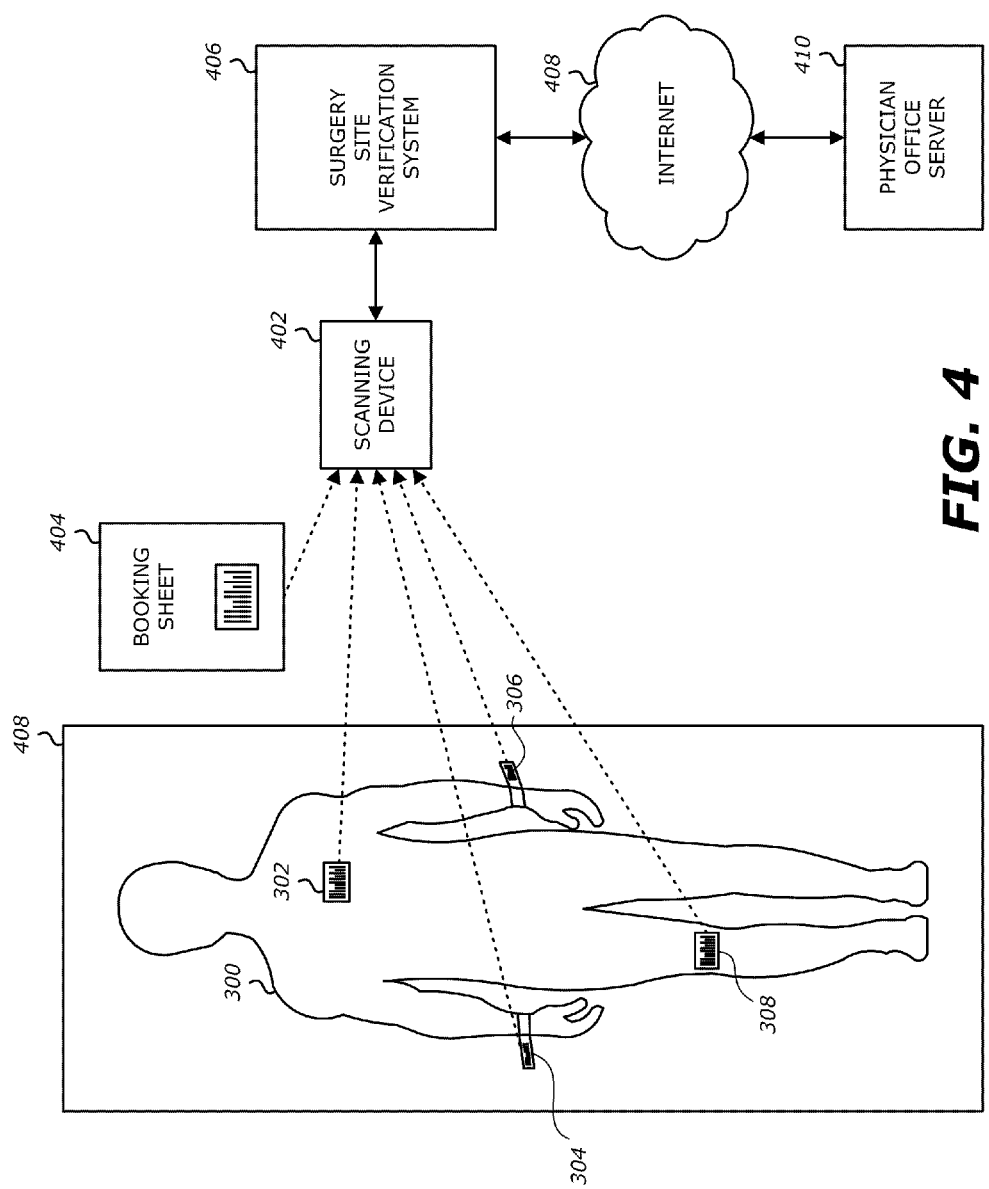
FIG. 4 is a block diagram illustrating one embodiment of a system for verifying a surgery site.

FIG. 4 is a block diagram illustrating one embodiment of a system for verifying a surgery site. The body of the patient 300 is placed on an operating table 408. Tags and stickers 302, 304, 306, 308 have been affixed to the body of the patient as previously described with respect to FIGS. 3A, 3B, and 3C. In the pre-operating room or operating room, a scanning device 402, for example, a handheld barcode reader scans and reads barcodes from booking sheet 404, barcode tags 302, 304, 306, and 308. In another embodiment, scanning device 402 includes means for determining an orientation of the scanning device with respect to a fixed reference (e.g. surgery verification site system 406). For example, scanning device 402 includes a gyroscope. Scanning device 402 communicates (wired or wirelessly) with a surgery site verification system 406.

In one embodiment, scanning device 402 requests a user (surgeon, nurse, or staff) to scan the barcode on the operating room booking sheet 404 associated with patient 300. Scanning device 402 may then display some or all of the information retrieved from the operating room booking sheet 404. The user may then verify whether the booking sheet is associated the patient by comparing an identification tag on the patient with the retrieved information from scanning device 402. In one embodiment, some or all of the retrieved information is displayed on another display device (monitor or tv) in or outside the operating room so that other hospital staff can also view the retrieved information. In another embodiment, the retrieved information can also be compared to the surgery room and/or surgery tools and accessories present in the surgery room.

Scanning device 402 may then request the user to scan heart barcode tag 302. In another embodiment, surgery site verification system 406 may further validate whether the scanned heart barcode tag 302 corresponds to a pre-identified heart barcode. In other words, surgery site verification system 406 verifies that the user scanned the barcode that he/she is supposed to scan.

Scanning device 402 may then request the user to scan a barcode on a wrist tag located on the same or opposite side as the heart barcode 302. Surgery site verification system 406 verifies that the scanned barcode is from the wrist tag identified to be on the same or opposite side as the heart based on data from booking sheet 404. In one embodiment, surgery site verification system 406 receives data about the patient by scanning a barcode on booking sheet 404. In another embodiment, surgery site verification system 406 receives data from another computer system, such as a physician's office server or an imaging server through a network of computers 408 (e.g. the Internet). For example, at a physician's office, the physician marks the location of the surgery on a computer. The information is then sent electronically to the hospital and loaded in the scanning device 402 or surgery site verification system 406 through the hospital network. On the day of the surgery, scanning device 402 and surgery site verification system 406 already contain the patient information and thus there would be no need to scan operating booking sheet 404.

If the correct wrist tag has been scanned, surgery site verification system 406 or scanning device 402 may notify the user to proceed. An audio and/or visual message may be displayed on scanning device 402, surgery site verification system 406, or another output device (not shown). If the wrong wrist tag has been scanned, surgery site verification system 406 or scanning device 402 warns the user to stop the surgery procedure. An audio (alarm) and/or visual message (e.g. red flashing lights or "you must stop. An error condition exists") may be displayed on scanning device 402, surgery site verification system 406, or another output device (not shown).

Scanning device 402 may then request the user to scan the surgery location barcode 308. In another embodiment, surgery site verification system 406 may further validate whether the scanned surgery location barcode 308 corresponds to the pre-defined surgery barcode. In other words, surgery site verification system 406 verifies that the user scanned the barcode that he/she is supposed to scan.

Scanning device 402 may then request the user to scan a barcode on a wrist tag located on the same or opposite side as surgery location barcode 308. Surgery site verification system 406 verifies that the scanned barcode is from the wrist tag identified to be on the same or opposite side as the surgery location barcode 308 based on data from booking sheet 404.

If the correct wrist tag has been scanned, surgery site verification system 406 or scanning device 402 may notify the user to proceed. An audio and/or visual message may be displayed on scanning device 402, surgery site verification system 406, or another output device (not shown). If the wrong wrist tag has been scanned, surgery site verification system 406 or scanning device 402 warns the user to stop the surgery procedure. An audio (alarm) and/or visual message (e.g. red flashing lights or "you must stop. An error condition exists") may be displayed on scanning device 402, surgery site verification system 406, or another output device (not shown).

In another embodiment, surgery location barcode sticker 308 may be used to identify a location on which a medical procedure is to be performed. The medical procedure is not limited to surgery, but also includes other surgical and non-surgical medical procedures such as filling a tooth cavity at a dentist, removing a tooth, examining an eye or ear, putting a cast on a limb, acupuncture on a hand, performing a CT scan or X ray on a body part, etc . . . .

In another embodiment, surgery site verification system 406 compares data from surgery location barcode sticker 308 with data with the barcode from booking sheet 404 to verify that the nature of the medical procedure is correct. If the data do not match, surgery site verification system 406 issues a warning notification.

Figure 5:
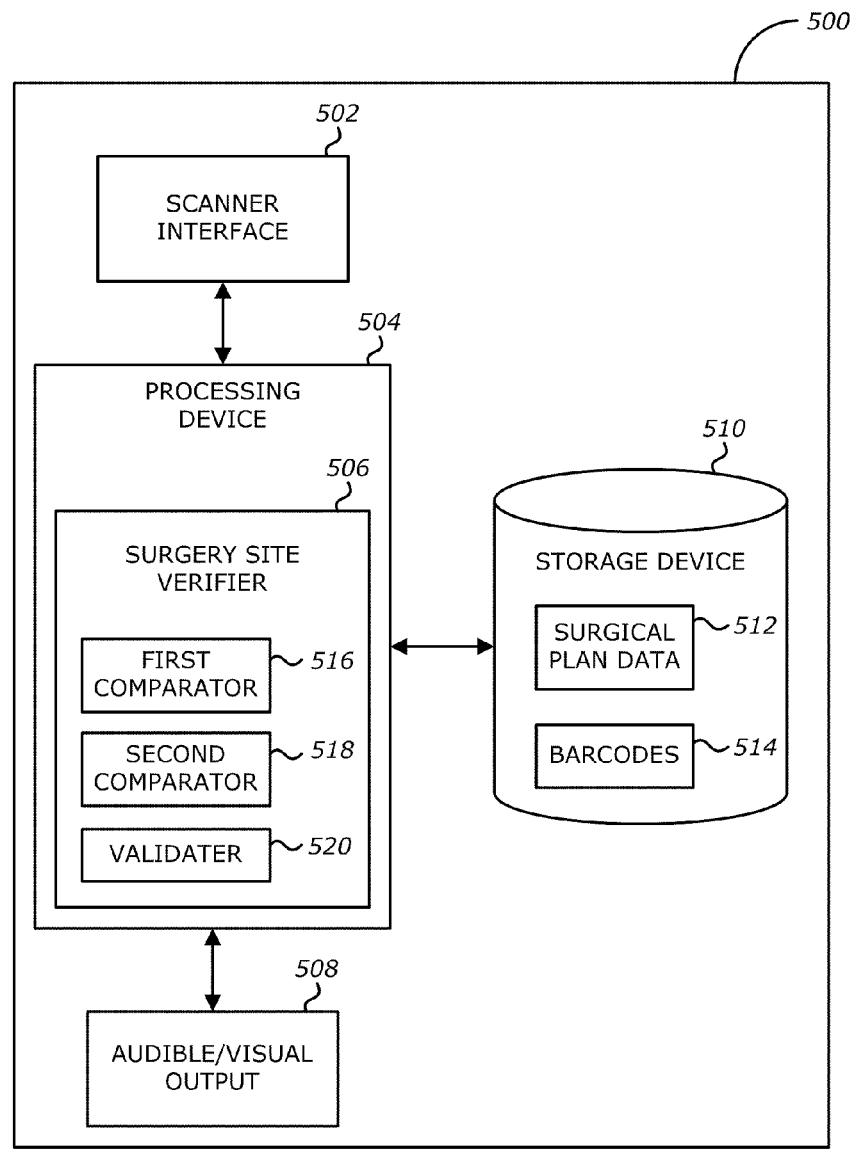
FIG. 5 is a block diagram illustrating one embodiment of a surgery site verification device.

FIG. 5 is a block diagram illustrating one embodiment of a surgery site verification device 500. A scanner interface 502 enables device 500 to communicate wirelessly or with wire to a handheld scanner device. Scanner interface 502 translates a scanned barcode into data and communicates the data to processing device 504 for further computation. In one embodiment, processing device 504 includes a surgery site verifier 506 configured to verify the validity of a planned surgery site. Surgery site verifier 506 is configured to receive surgical plan data 512 associated with the patient from scanning a booking sheet. The surgical plan data may be stored in a storage device 510 coupled to processing device 504. Scanned barcodes 514 with respect to surgery location, heart location, left or right side location may also be stored in storage device 510. Surgery site verifier 506 compares the surgical plan data 512 with scanned barcodes 514 to verify the validity of the planned surgical site.

In one embodiment, surgery site verifier 506 includes a first comparator 516, a second comparator 518, and a surgical site validater 520. First comparator 516 is configured to determine whether the scanned heart barcode is on the same or opposite side as the scanned surgery location barcode.

Second comparator 518 determines whether the scanned heart barcode is supposed to be on the same or opposite side as the scanned surgery location barcode based on the surgical plan data 512 associated with the patient retrieved from booking sheet.

Surgical site validater 520 is configured to validate the planned surgical site based on whether the output of the first comparator matches the output of the second comparator.

An audio/visual warning output device 508 (e.g. alarm or siren) communicates with surgical site validater 520 to issue an audio and/or visual warning when surgical site validater 520 cannot validate the planned surgical site.

FIG. 5 illustrates a diagrammatic representation of a machine in the exemplary form of a computer system 500 within which a set of instructions, for causing the machine to perform any one or more of the methodologies discussed herein, may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

In one embodiment, the exemplary computer system 500 includes processing device 504, a main memory (e.g., read-only memory (ROM), flash memory, dynamic random access memory (DRAM) such as synchronous DRAM (SDRAM), a static memory (e.g., flash memory, static random access memory (SRAM), etc.), and data storage device 510, which communicate with each other via a bus.

Processing device 504 represents one or more general-purpose processing devices such as a microprocessor, central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 504 may also be one or more special-purpose processing devices such as an application specific integrated circuit (ASIC), a field programmable gate array (FPGA), a digital signal processor (DSP), network processor, or the like. The processing device 504 is configured to execute module 506 for performing the operations and steps discussed herein with. In one embodiment, module 506 may be include hardware or software or a combination of both.

The computer system 500 may further include a network interface device, a video display unit (e.g., a liquid crystal display (LCD) or a cathode ray tube (CRT)), an alphanumeric input device (e.g., a keyboard), a cursor control device (e.g., a mouse), and a signal generation device 508 (e.g., a speaker).

Storage device 510 may include a computer-accessible storage medium on which is stored one or more sets of instructions (e.g., surgery site verifier software 506) embodying any one or more of the methodologies or functions described herein. The software 506 may also reside, completely or at least partially, within the main memory and/or within the processing device 504 during execution thereof by the computer system 500, the main memory and the processing device 504 also constituting computer-accessible storage media. The software 506 may further be transmitted or received over a network via the network interface device.

The computer-accessible storage medium may also be used to store a surgery site verifier 506 as presently described. Surgery site verifier 506 may also be stored in other sections of computer system 500, such as static memory.

While the computer-accessible storage medium is shown in an exemplary embodiment to be a single medium, the term "computer-accessible storage medium" should be taken to include a single medium or multiple media (e.g., a centralized or distributed database, and/or associated caches and servers) that store the one or more sets of instructions. The term "computer-accessible storage medium" shall also be taken to include any medium that is capable of storing, encoding or carrying a set of instructions for execution by the machine and that cause the machine to perform any one or more of the methodologies of the present invention. The term "computer-accessible storage medium" shall accordingly be taken to include, but not be limited to, solid-state memories, optical and magnetic media.

Figure 6:
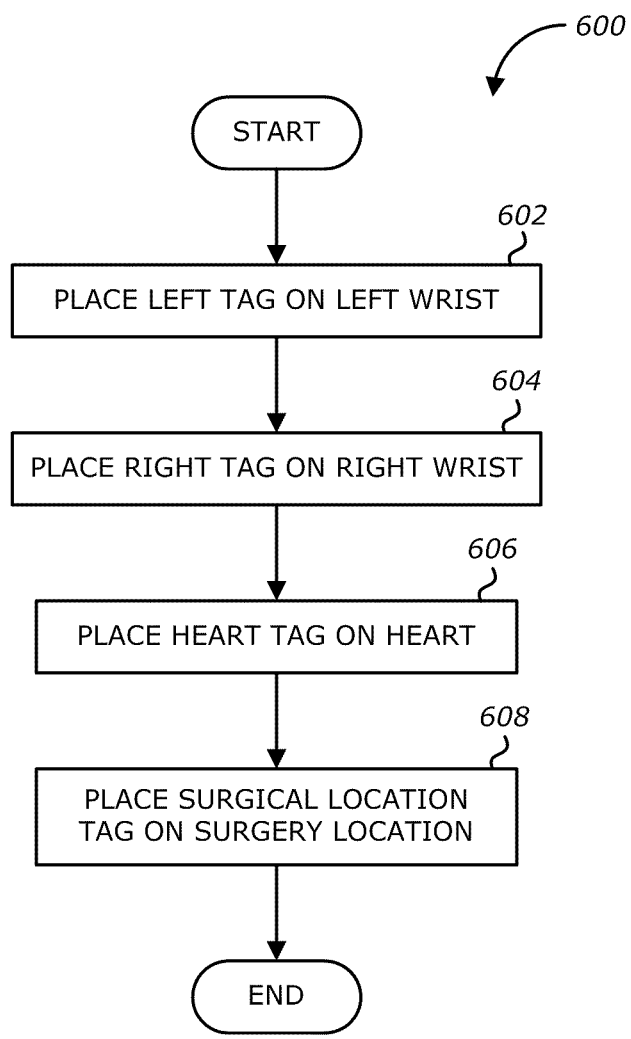
FIG. 6 is a flow diagram illustrating one embodiment of a method for placing barcode tags on a body of a patient.

FIG. 6 is a flow diagram illustrating one embodiment of a method for placing barcode tags on a body of a patient. At 602, a nurse or staff places the left barcode tag on the left wrist of a patient. At 604, the nurse places the right barcode tag on the right wrist of the patient. At 606, the nurse places the heart location barcode tag on a location adjacent to the heart on the chest of the patient. At 608, the nurse places the surgical location barcode tag on the surgery site on the body of the patient.

Figure 7:
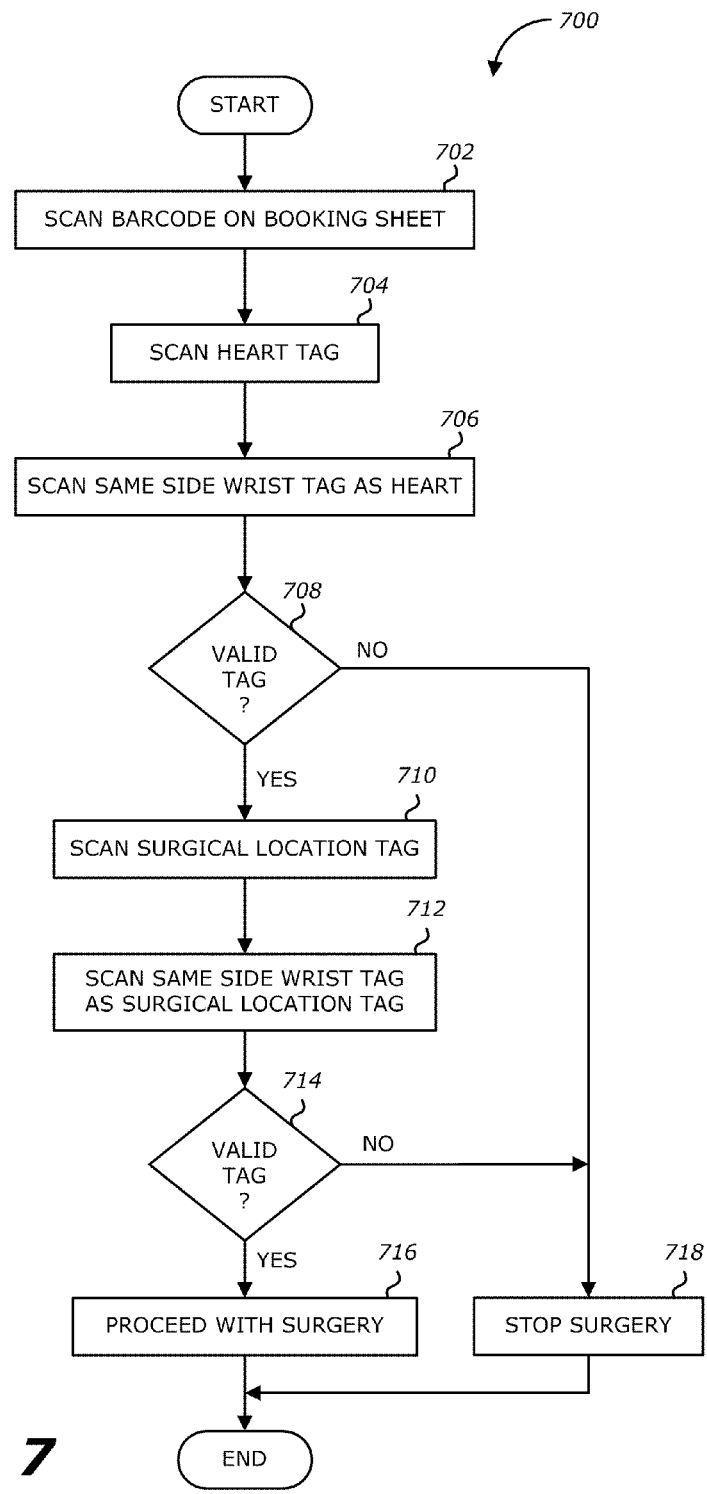
FIG. 7 is a flow diagram illustrating one embodiment of a method for verifying a surgery site using barcode tags on a body of a patient.

FIG. 7 is a flow diagram illustrating one embodiment of a method for verifying a surgery site using barcode tags on a body of a patient. At 702, a user scans a booking sheet barcode on an operating room booking sheet. At 704, the user scans a heart barcode on the heart location on the body of the patient. At 706, the user scans a wrist barcode on a wrist on a same or opposite side of the heart of the patient as instructed by the system. At 708, the system determines whether the scanned wrist barcode is valid. The system is able to determine whether a specific wrist barcode is to be on the same or opposite side of the heart based on data from the scanned booking sheet. If the scanned wrist barcode does not match with the data from the scanned booking sheet, the user is notified to stop the surgery at 718.

At 710, the user scans the surgery location barcode tag. At 712, the user is instructed by the system to scan a wrist barcode located on a same side or opposite side of the body of the patient. At 714, the system determines whether the scanned wrist barcode is valid. The system is able to determine whether a specific wrist barcode is to be on the same or opposite side of the surgery site based on data from the scanned booking sheet. If the scanned wrist barcode does not match with the data from the scanned booking sheet, the user is notified to stop the surgery at 718.

If the system determines that all scanned barcodes are valid, the system notifies the user to proceed at 716.

Figure 8:
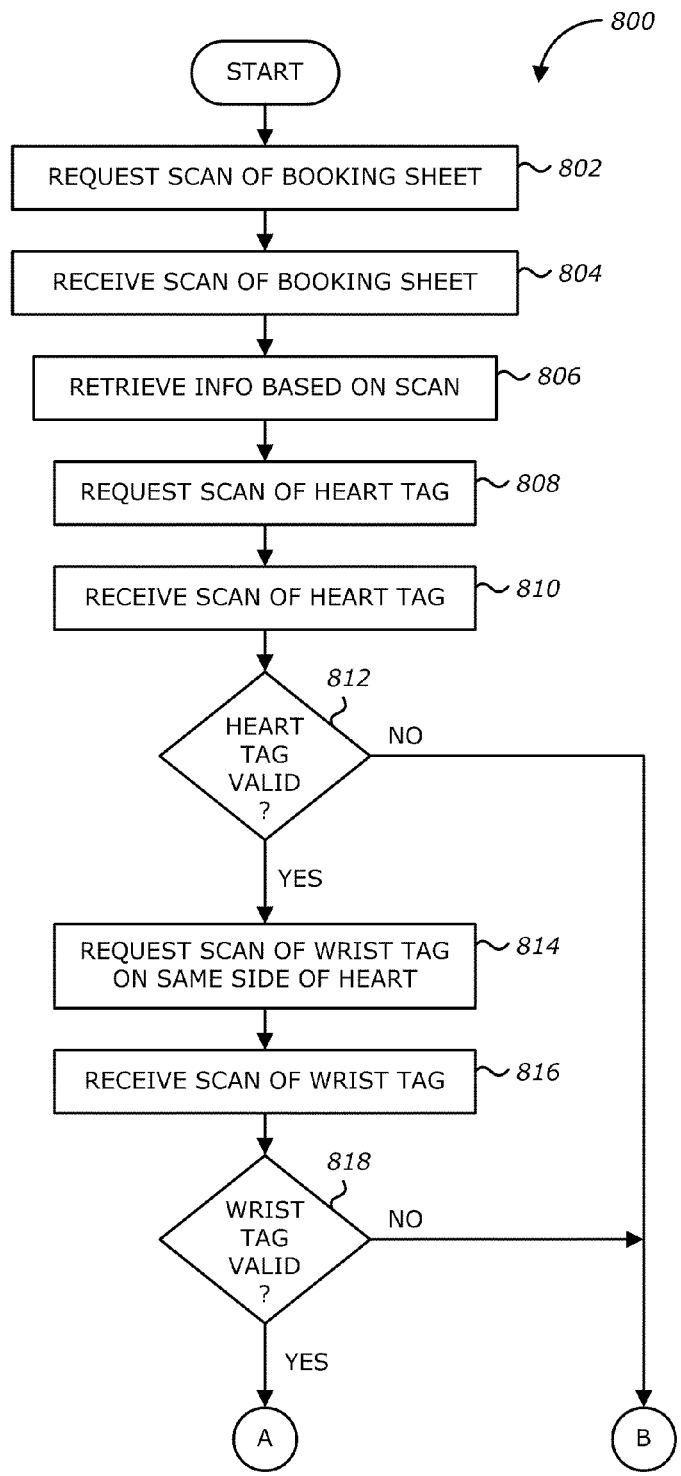
FIG. 8 is a flow diagram illustrating another embodiment of a method for verifying a surgery site using barcode tags on a body of a patient.
Figure 8:
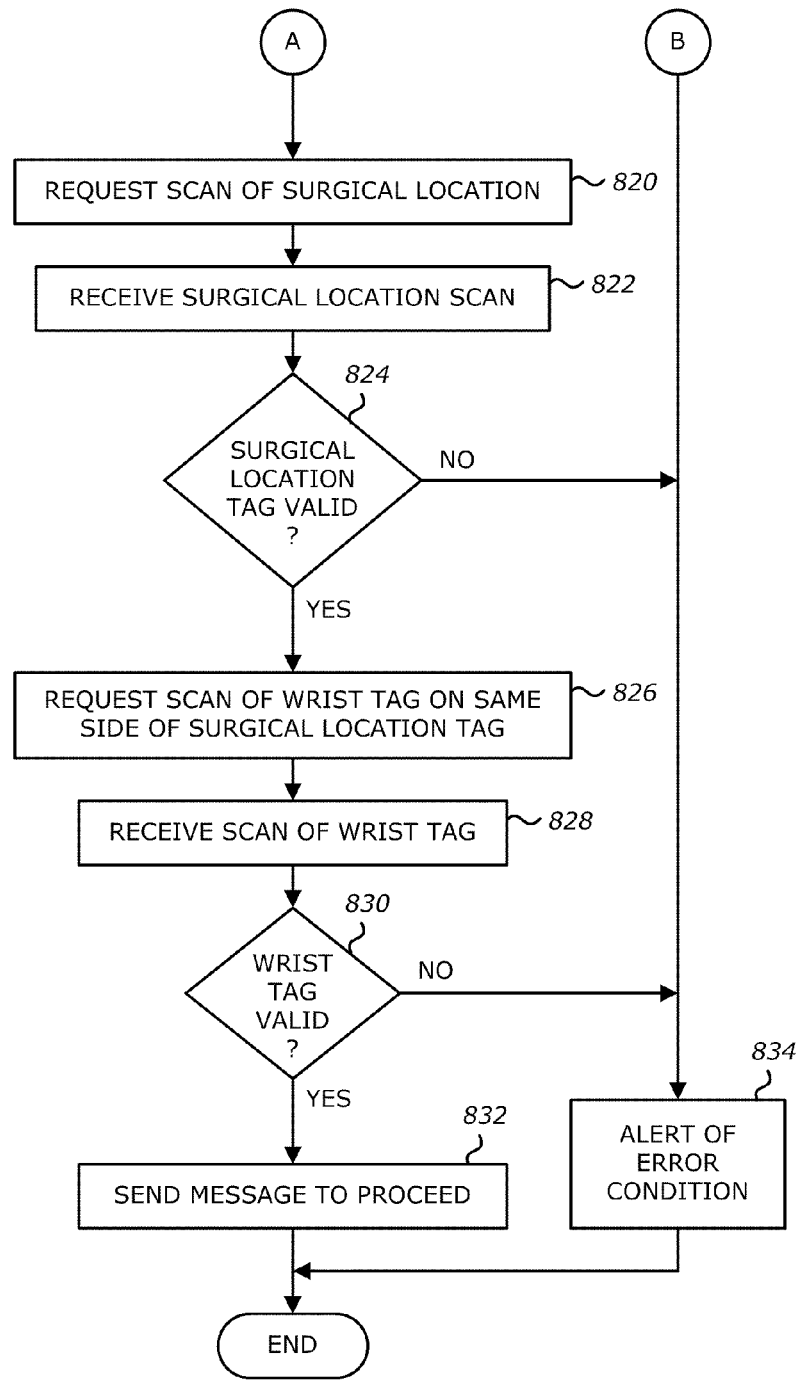

FIG. 8 is a flow diagram illustrating another embodiment of a method for verifying a surgery site using barcode tags on a body of a patient. At 802, the system requests a user to scan the operating room booking sheet. At 804, the system reads the barcode from the booking sheet. At 806, the system retrieves patient information based on a scan of the booking sheet. At 808, the system requests the user to scan the heart location barcode tag. At 810, the system reads the heart location barcode. At 812, the system determines whether the heart location barcode is valid. At 814, the system requests the user to scan the wrist barcode tag located on the same side as the heart of the patient. At 816, the system reads the wrist barcode. At 818, the system determines whether the wrist barcode is valid. At 820, the system requests the user to scan the surgical location barcode tag. At 822, the system reads the surgical location barcode. At 824, the system determines whether the surgical location barcode is valid. At 826, the system requests the user to scan the wrist barcode tag located on the same side as the surgery location of the patient. At 828, the system reads the wrist barcode. At 830, the system determines whether the wrist barcode is valid.

If the system determines that all scanned barcodes are valid, the system notifies the user to proceed at 832. If the system cannot validate any of the scanned barcode, the system alerts the user of the error condition at 834.

Figure 9:
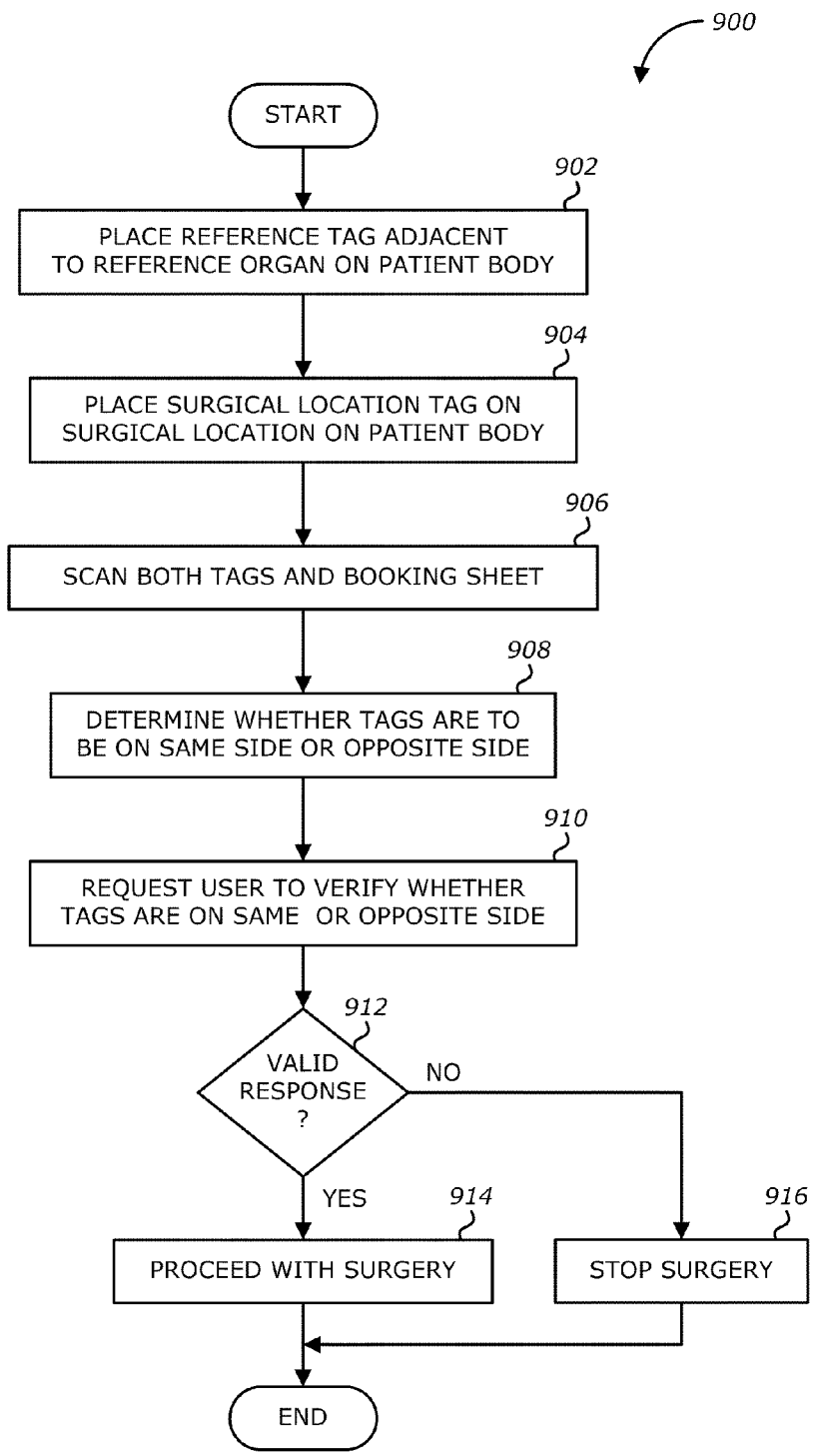
FIG. 9 is a flow diagram illustrating another embodiment of a method for verifying a surgery site using barcode tags on a body of a patient.

FIG. 9 is a flow diagram illustrating another embodiment of a method for verifying a surgery site using barcode tags on a body of a patient. At 902, a reference tag is placed adjacent to a reference organ on a body of a patient. At 904, a surgery location tag is placed on a surgery location on the body of the patient. At 906, both barcode tags are scanned along with the operating room booking sheet associated with the patient. At 908, the system determines whether the barcode tags are supposed to be on the same or opposite side of the body. At 910, the system requests the user to verify whether the tags are on the same side. At 912 if the user response is correct, the system notifies the user to proceed with the surgery at 914. Otherwise, the system notifies the user to stop the process at 916.

Figure 10:
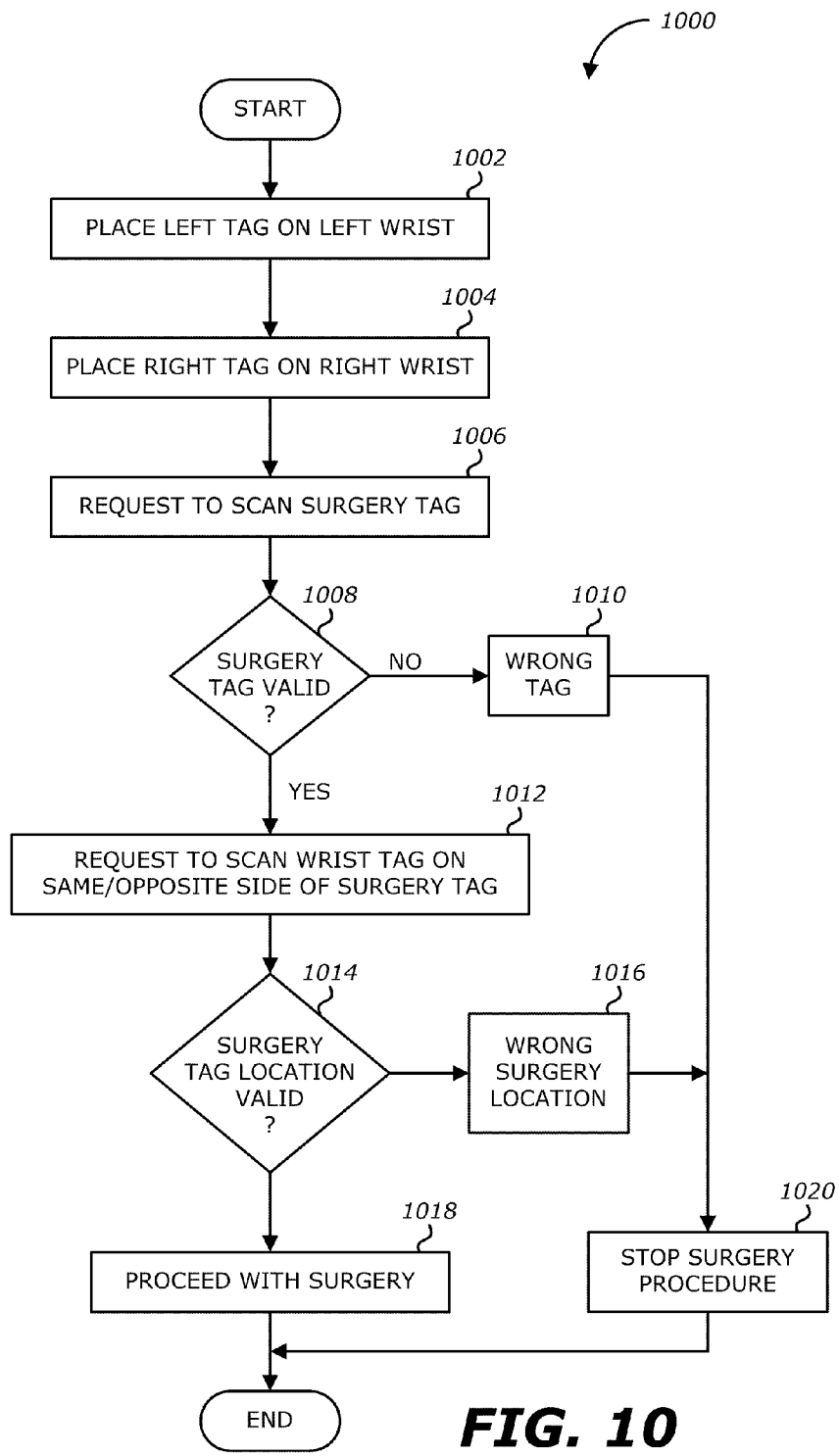
FIG. 10 is a flow diagram illustrating another embodiment of a method for verifying a surgery site using barcode tags on a body of a patient.

FIG. 10 is a flow diagram illustrating another embodiment of a method for verifying a surgery site using barcode tags on a body of a patient. It is assumed that the surgery location barcode tag is placed on the planned surgery site. At 1002, the left barcode wrist tag is placed on the left wrist of the patient. At 1004, the right barcode wrist tag is placed on the right wrist of the patient. At 1006, the system requests the user to scan the surgery location barcode tag. If the wrong barcode is detected at 1010, the system notifies the user to stop the surgery procedure at 1020.

At 1012, the system requests the user to scan the wrist barcode tag on the same/opposite side of the surgery location barcode tag. At 1014, the system determines whether the surgery location barcode tag is valid based on data from a booking sheet associated with the patient. If the surgery location barcode is valid, the system notifies the user to proceed with the surgery at 1018. If the system determines that the surgery location barcode tag is not valid, it notifies the user at 1020.

In the above description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "reading" or "verifying" or "validating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system comprising:
   a reader configured to read a first and second machine readable marking,
   wherein the first machine readable marking associated with a medical procedure site on a body of a patient is placed on a planned medical procedure site on the body of the patient, wherein the second machine readable marking is associated with a pre-identified reference point placed on the corresponding pre-identified reference point; and
   validater coupled to the reader, the validater configured to receive medical procedure plan data associated with the patient and to compare the medical procedure plan data with the first and second machine readable marking to verify the validity of the planned medical procedure
   wherein the pre-identified reference point includes location of an organ of the body of the patient without reference to a left or right side of the patient.

2. The system of claim 1 wherein the validater comprises:
   a first comparator configured to determine whether the first machine readable marking is on the same or opposite side as the second machine readable marking;
   a second comparator configured to determine whether the first machine readable marking is to be on the same or opposite side as the second machine readable marking based on the medical procedure plan data associated with the patient;
   a medical procedure site validater configured to validate the planned medical procedure site based on the first comparator and the second comparator; and
   an audio or visual warning device coupled to the medical procedure site validate, the audio or visual warning device configured to issue an audio or visual warning when the planned medical procedure site is not validated.

3. The system of claim 2 wherein the medical procedure site validater is configured to validate the planned medical procedure site only when an output of the first comparator corresponds to an output of the second comparator.

4. The system of claim 1 wherein the pre-identified reference point includes a reference point on left or right side of the patient.

5. The system of claim 1 wherein the reference point includes a part of the body of the patient located on a left or right side of the patient.

6. The system of claim 1 wherein the medical procedure plan data associated with the patient includes data from a booking sheet or data from a computer system, the booking sheet comprising an identification of the patient, a location of the medical procedure site on the body of the patient, and a medical procedure for the patient.

7. The system of claim 1 Wherein the first or second machine readable marking includes a barcode, wherein the reader includes a barcode scanner.

8. The system of claim 1 wherein the first or second machine readable marking includes a Radio Frequency identification (RFID) tag, wherein the reader includes an RFID scanner.

9. The system of claim 1 further comprising: a third machine readable marking placed, on a left limb of the patient: and a fourth machine readable marking placed on a right limb of the patient, a first comparator of the validater configured to determine whether the third or fourth machine readable marking is placed on a same or opposite side of the first machine readable marking along a vertical axis funned along a vertebrae of the body of the patient; a second comparator of the validater configured to determined whether the third or fourth machine readable marking is placed on a same or opposite side of the second machine readable marking along the vertical axis; and a medical procedure site validater configured to validate the planned medical procedure site based on whether an output of the first and second comparator corresponds to the medical procedure plan data associated the patient.

10. The system of claim 9 wherein the reader is configured to request a user to scan a machine readable marking placed on the same or opposite side of the first or second machine readable marking.

11. The system of claim 1 wherein the validater is configured to determine whether the first machine readable marking corresponds to a machine readable marking of the medical procedure site associated with the booking sheet, whether the second machine readable marking corresponds to the pre-identified reference point.

12. A method for managing a medical procedure site on a patient comprising: receiving a medical procedure plan data associated with the patient;
   reading a first machine readable marking associated with the medical procedure site on a body of the patient with a reader, the first machine readable marking placed on a planned medical procedure site on the body of the patient;
   reading a second machine readable marking associated with a pre-identified reference point with the reader, the second machine readable marking placed on the corresponding pre-identified reference point; and verifying the validity of the planned medical procedure based on the medical procedure plan data associated with the patient and the reading of the first and second machine readable marking wherein the pre-identified reference point includes location of an organ of the body of the patient without reference to a left or right side of the patient.

13. The method of claim 12 further comprising:

determining whether the first machine readable marking is on the same opposite side as the second machine readable marking;

determining whether the first machine readable marking is to be on the same or opposite side as the second machine readable marking based on the medical procedure plan data associated with the patient;

validating the planned medical procedure site based on the first comparator and the second comparator; and issuing an auditory or visual warning when the planned medical procedure site is not validated.

14. The method of claim 13 farther comprising: validating the planned medical procedure site only when the first and second machine readable marking are on a side consistent with the medical procedure plan data.

15. The method of claim 12 wherein the medical procedure plan data associated with the patient comprises an identification of the patient, a location of the medical procedure site on the body of the patient, and a medical procedure for the patient.

16. The method of claim 12 wherein the first or second machine readable marking includes a barcode, and the reader includes a barcode scanner.

17. The method of claim 12 wherein the first or second machine readable marking includes a Radio Frequency Identification (RFID) tag, and the reader includes an (RFID) scanner.

18. The method of claim 12 further comprising:

reading a third machine readable marking placed on a left limb of the patient; reading a fourth machine readable marking placed on a right limb of the patient, determining whether the third or fourth machine readable marking is placed on a same or opposite side of the first machine readable marking along a vertical axis formed along a vertebrae of the body of the patient;

determining whether the third or fourth machine readable marking is placed on a same or opposite side of the second machine readable marking along the vertical axis; and validating the planned medical procedure site based on whether the third or fourth machine readable marking is on a side relative to the first or second machine readable marking consistent with the medical procedure plan data associated the patient.

19. The method of claim 18 further comprising; requesting a user to scan a machine readable marking placed on the same or opposite side of the first or second machine readable marking.

20. The method of claim 12 further comprising: determining, whether the first machine readable marking corresponds to a machine readable marking of the medical procedure site associated with the booking sheet; and determining whether the second machine readable marking corresponds to the pre-identified reference point.

21. A computer-readable storage medium, having instructions stored therein, which when executed, cause a computer system to perform a method comprising:

receiving a medical procedure plan data associated with the patient;

reading a first machine readable marking associated with the medical procedure site on a body of the patient with a reader, the first machine readable marking placed on a planned medical procedure site on the body of the patient;

reading a second machine readable marking, associated with a pre-identified reference point with the reader, the second machine readable marking placed on the corresponding pre-identified reference point; and verifying the validity of the planned medical procedure based on the medical procedure plan data associated with the patient and the reading of the first and second machine readable marking;

determining whether the first machine readable marking is on the same or opposite side as the second machine readable marking;

determining whether the first machine readable marking is to be on the same or opposite side as the second machine readable marking based on the medical procedure plan data associated with the patient;

validating the planned medical procedure site based on the first comparator and the second comparator; and issuing an auditory or visual warning when the planned medical procedure site is not validated.

22. The computer-readable storage medium of claim 21 wherein the method further comprises: validating the planned medical procedure site only when the first and second machine readable marking are on a side consistent with the medical procedure plan data.

23. The computer-readable storage medium of claim 21 wherein the medical procedure plan data associated with the patient comprises an identification of the patient, a location of the medical procedure site on the body of the patient, and a medical procedure for the patient.

24. The computer-readable storage medium of claim 21 wherein the first or second machine readable marking includes a barcode, and the reader includes a barcode scanner.

25. The computer-readable storage medium of claim 21 wherein the first or second machine readable marking includes a Radio Frequency Identification (RFID) tag, and the reader includes an RFID scanner.

26. The computer-readable storage medium of claim 21 wherein the method further comprises:

reading a thud machine readable marking placed on a left limb of the patient reading a fourth machine readable marking placed on a right limb of the patient, determining whether the third or fourth machine readable marking is placed on a same or opposite side of the first machine readable marking along a vertical axis formed along a vertebrae of the body of the patient; determining whether the third or fourth machine readable marking is placed on a same or opposite side of the second machine readable marking along the vertical axis; and validating the planned medical procedure site based on whether the third or fourth machine readable marking is on a side relative to the first or second machine readable marking consistent with the medical procedure plan data associated the patient.

27. The computer-readable storage medium of claim 21 wherein the method further comprises: requesting a user to scan a machine readable marking placed on the same or opposite side of the first or second machine readable marking.

28. The computer-readable storage medium of claim 21 wherein the method further comprises: determining whether the is. readable marking corresponds to a machine readable marking of the medical procedure site associated with the booking sheet; and determining whether the second machine readable marking corresponds to the pre-identified reference point.

* * * * *